US007025749B2

(12) United States Patent
Propp

(10) Patent No.: US 7,025,749 B2
(45) Date of Patent: Apr. 11, 2006

(54) JUGULAR AND SUBCLAVIAN ACCESS SITE DRESSING AND METHOD

(75) Inventor: Donald J. Propp, Dewitt, MI (US)

(73) Assignee: Tri-State Hospital Supply Corporation, Howell, MI (US)

( * ) Notice: Subject to any disclaimer, the term of this patent is extended or adjusted under 35 U.S.C. 154(b) by 26 days.

(21) Appl. No.: 10/851,401

(22) Filed: May 21, 2004

(65) Prior Publication Data

US 2005/0261623 A1 Nov. 24, 2005

(51) Int. Cl.
*A61M 5/32* (2006.01)
(52) U.S. Cl. .................................... 604/180
(58) Field of Classification Search ............. 604/174, 604/180; 128/DIG. 26
See application file for complete search history.

(56) References Cited

U.S. PATENT DOCUMENTS

| | | | | |
|---|---|---|---|---|
| 4,669,458 A | * | 6/1987 | Abraham et al. | 128/846 |
| 5,304,146 A | * | 4/1994 | Johnson et al. | 604/180 |
| 5,520,629 A | * | 5/1996 | Heinecke et al. | 602/57 |
| 6,124,521 A | * | 9/2000 | Roberts | 602/54 |
| 6,273,873 B1 | * | 8/2001 | Fleischer | 604/174 |
| 6,841,715 B1 | * | 1/2005 | Roberts | 602/54 |
| 2004/0143220 A1 | * | 7/2004 | Worthley | 604/174 |

OTHER PUBLICATIONS

SorbaView 2000 Window Dressing, Tri-State Hospital Supply Corporation, Apr. 14, 2004.*

* cited by examiner

*Primary Examiner*—Sharon Kennedy
(74) *Attorney, Agent, or Firm*—Fildes & Outland, P.C.

(57) ABSTRACT

A jugular and subclavian access site window dressing includes anchoring and closure members. The anchoring member has an axis dividing the anchoring member into first and second portions. The anchoring member includes a fabric layer having an adhesive side, an opposite non-adhesive side, and an opening therein bounded by an edge. A transparent film layer, having an adhesive skin adhering side and an opposite non-adhesive side, closes the fabric layer opening. The film layer is larger than the opening in all directions. The film layer non-adhesive side is adhered onto the adhesive side of the fabric layer around the opening and extends beyond the edge of the opening. The closure member has an axis dividing the closure member into first and second portions and includes a fabric layer having opposing adhesive and non-adhesive sides. The closure member is adapted to overlie and close an end of the anchoring member.

39 Claims, 6 Drawing Sheets

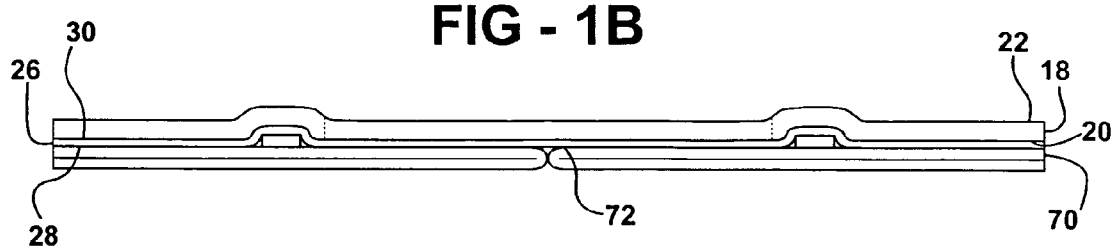
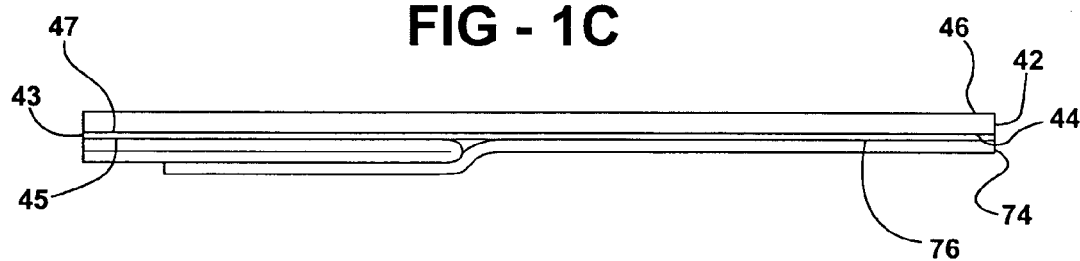
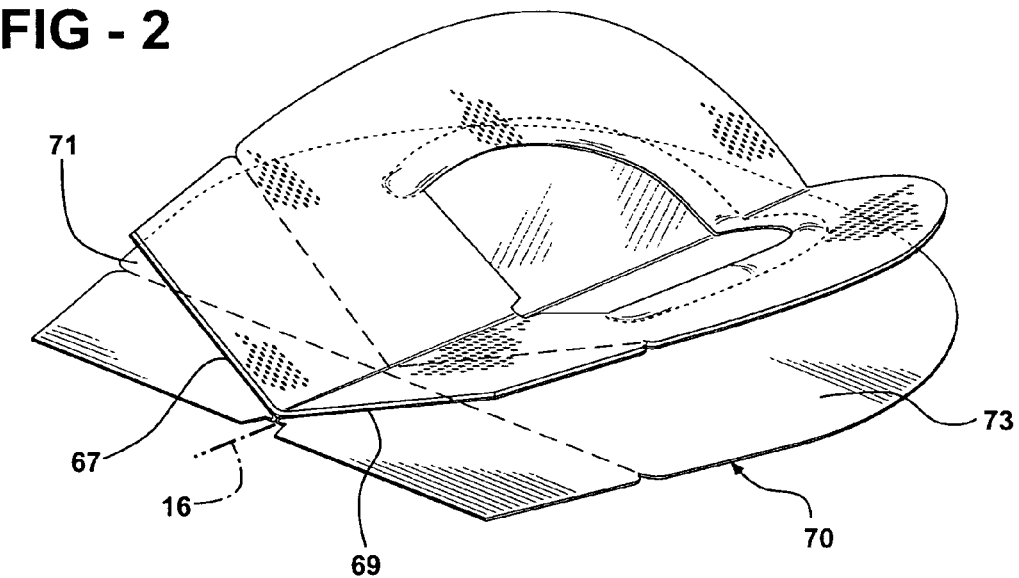
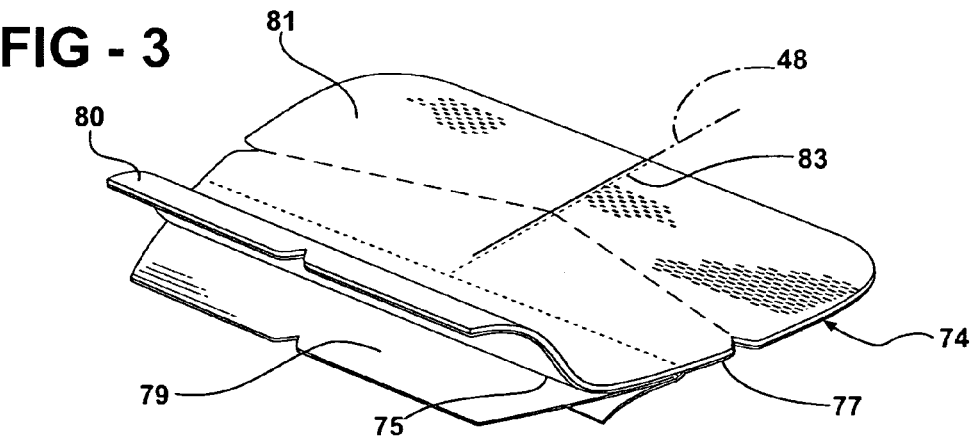

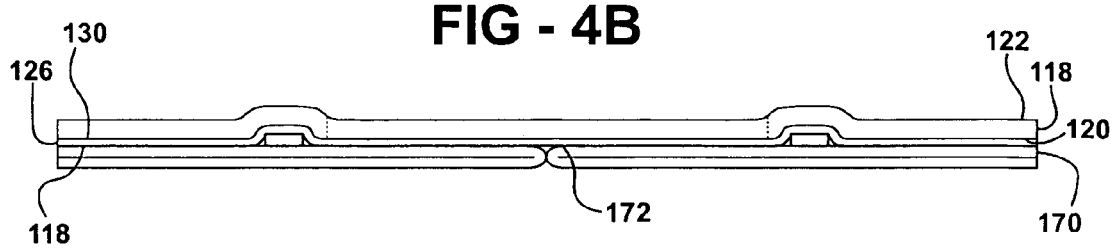
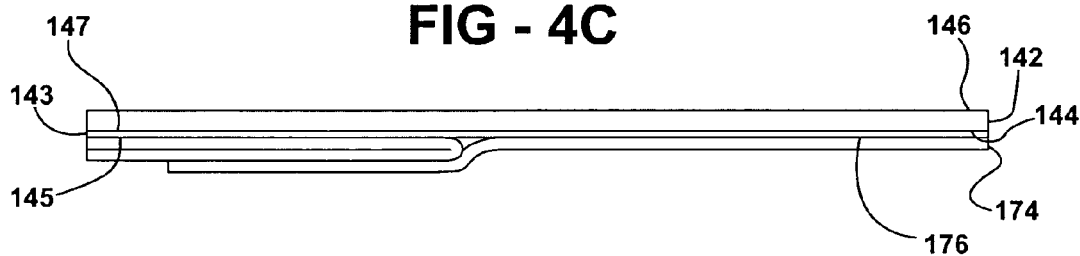
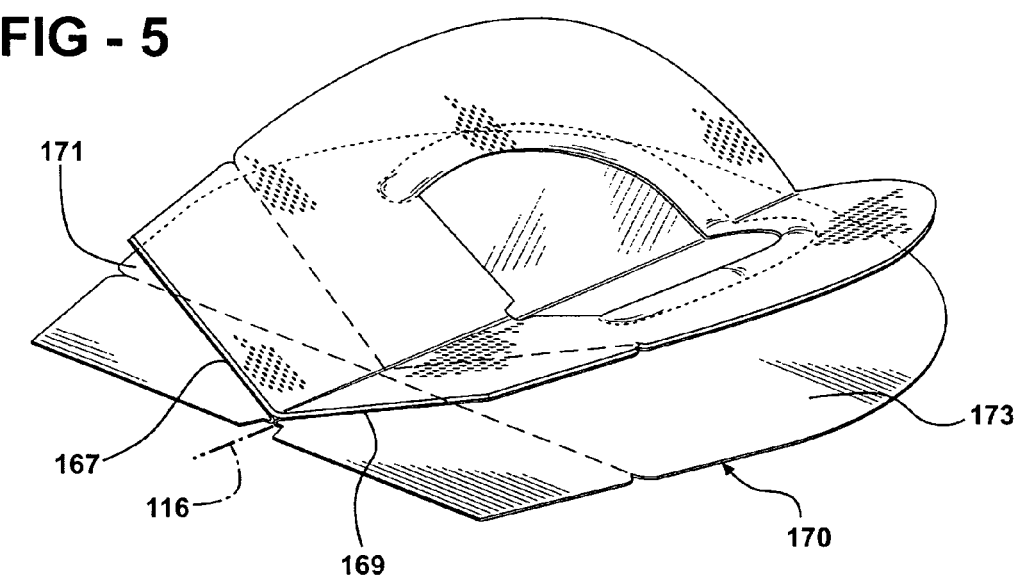
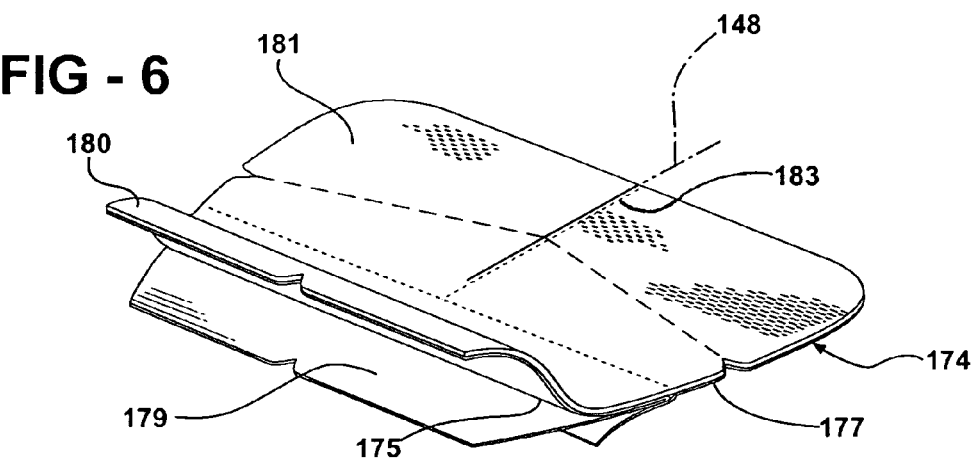

JUGULAR AND SUBCLAVIAN ACCESS SITE DRESSING AND METHOD

TECHNICAL FIELD

This invention relates to dermal dressings for the protection of jugular or subclavian catheter access sites, and more particularly to a window dressing for securing introducer sheaths and catheters at and around a jugular or subclavian access site.

BACKGROUND OF THE INVENTION

It is known in the art relating to dressings for indwelling catheter access sites to use protective bandage tape or clear film product alternatives that use non-sensitizing hypoallergenic adhesives to cover all or part of the indwelling catheter access sites. Some dressings combine non-woven tape and absorbent gauze-like materials which have skin-mating surfaces of non-adherent film to reduce the effect of adhesive stripping caused by the dressing removal. The absorbency and bacterial barrier of the pad typically varies minimally from one manufacturer to another, but this type of dressing is least occlusive to moisture vapor.

One known dressing system includes an opaque pad for adhesive placement over an access site and an adhesive strip, for adhesive securement to the skin of a patient under a catheter tube as it emerges from underneath the pad, and between the skin and the pad along the edges of the pad in opposite directions from the tube exit location.

In known prior art access site dressings, a side arm of an introducer sheath, which is usually at a 60 degree or 90 degree angle to the introducer sheath secured by the dressing, and other medical tubing and connectors, and stresses imparted thereto, can cause separation of the dressing from a patient's skin. For example, when a patient moves his or her head, the side arm or other tubing acts as a lever and tears loose the dressing. This is undesirable because a patient will often move his or her head and the dressing is ineffective if it releases from the patient's skin. Also, the side arm tends not to stay flat against a patient's body but instead projects or lifts up off the body, which further loosens the dressing.

Further, known prior art access site dressings have not been able to accommodate all of the potential combinations of medical tubing that can exist at an access site. For example, during open heart and/or thoracic surgery, an introducer sheath alone or an introducer sheath along with either a single, double, or triple lumen central venous catheters (CVC) may be present at an access site. Alternatively, there may be an introducer sheath in combination with a pulmonary artery catheter (PAC) (for example a Swan-Ganz or similar) or an introducer sheath in combination with a Swan-Ganz catheter along with either a single, double, or triple lumen CVC. Finally, after surgery in the operating room, the introducer sheath is usually removed within one to two days, but the CVC (either single, double, or triple lumen) may remain in the access site for up to seven or more days. The prior art dressings have been able to accommodate some of these combinations but no prior art dressing has been suitable for use with all of these possible combinations. Even those which do accommodate a few combinations often come loose from the skin within a day or less, and thus serve no useful clinical purpose.

Finally, for medical procedures involving an access site, either a right side or a left side access site may be used. It is preferable to use the right side access site, but in approximately 40% of the cases, it is necessary to use the left side access site. Prior art access site dressings are capable of being used on either the right hand side or the left hand side, however, they do not secure and protect the catheters and access sites, and come loose prematurely on either the left or right side.

SUMMARY OF THE INVENTION

The present invention provides a window dressing for a jugular or subclavian access site that avoids the deficiencies of the prior art. Specifically, the present invention provides a jugular and subclavian access site dressing that allows a patient to move his or her head or cause other movement and associated stresses without causing the dressing to release. The present invention also accommodates the side arm of an introducer sheath, that can accommodate various combinations of introducer sheaths and catheters, and that can be used on either a right or left access site.

More specifically, the present invention is a two-piece jugular and subclavian access site window dressing for the protection of a jugular or subclavian catheter access site, which is interchangeably usable on both a right or left access site. The dressing includes a anchoring member and a closure member. The anchoring member has an axis that divides the anchoring member into first and second portions. Optionally, the anchoring member axis may be an axis of symmetry. The anchoring member includes a fabric layer having an adhesive side, an opposite non-adhesive side, and an opening therein bounded by an edge, to allow access site viewing through the opening. The anchoring member also includes a transparent film layer that is larger than the opening in all directions, closing the opening in the anchoring member fabric layer. The transparent film layer has an adhesive skin adhering side and an opposite non-adhesive side. The film layer non-adhesive side is adhered onto the adhesive side of the anchoring member fabric layer around the opening such that the transparent film layer extends beyond the edge of the opening.

The closure member has an axis that divides the closure member into first and second portions. Optionally, the closure member axis may be an axis of symmetry. The closure member further includes a closure member fabric layer that has an adhesive side and an opposite non-adhesive side. The closure member is adapted to overlie and close an end of the anchoring member.

Optionally, the anchoring member fabric layer further may include symmetrically disposed perforation lines extending from an outer edge of the anchoring member fabric layer towards the anchoring member axis and being generally perpendicular to the anchoring member axis. Each perforation line may terminate before the anchoring member axis at a cross stop cut that is generally parallel to the anchoring member axis. The anchoring member may further include a generally C-shaped pad that is disposed along the edge of the opening, is symmetrically disposed about the anchoring member axis, and is adhered to the adhesive side of the film layer.

The closure member may include a film layer having an adhesive skin adhering side and an opposite non-adhesive side. The film layer non-adhesive side may be adhered onto the adhesive side of the closure member fabric layer. The closure member also may have symmetrically disposed perforation lines that extend angularly from an outer edge of the closure member towards the closure member axis and meet at a similar point along the closure member axis. The closure member furthermore may include a perforation line extending generally centrally from the outer edge of the closure member at a point located on the closure member axis, run along the closure member axis, and terminate near the center of the closure member at a closure member cross stop cut. The closure member cross stop cut may be generally perpendicular to the closure member axis. The closure member also may include a cut line that extends generally centrally from the outer edge of the closure member at a point located on the closure member axis opposite the point where the center perforation line begins, and ends at the closure member cross stop cut.

The closure member may also have a pad disposed about the closure member axis near the center of the closure member and adhered to the non-adhesive side of the closure member fabric layer. Alternatively, the pad may extend from one edge of the closure member to another edge of the closure member generally perpendicular to the closure member axis.

The dressing may further include notches along the outer edge of the anchoring member fabric layer that are disposed at ends of the anchoring member perforation lines opposite the anchoring member cross stop cuts. The anchoring member fabric layer also may have landmark notches disposed about the anchoring member axis that are located at both the outer edge of the anchoring member fabric layer and at an edge of the opening. The dressing furthermore may include notches along the outer edge of the closure member fabric layer that are disposed at ends of the closure member perforation lines and at the point on the closure member axis where the closure member center perforation line begins.

Furthermore, the dressing may include an anchoring member release liner that has a tackless side that contacts the adhesive side of the anchoring member fabric layer and the adhesive side of the anchoring member film layer, and the surface of the anchoring member release liner that contacts the adhesive side of the anchoring member film layer may generally correspond in size and shape to the anchoring member fabric layer. The anchoring member release liner may further have a first piece and a second piece, the first and second pieces being folded along the anchor member axis. The anchoring member release liner may further include first and second tabs formed by the folds, whereby one of the pieces may be released from the anchoring member without tampering with the other of the pieces.

The dressing further may include a closure member release liner that has a tackless side contacting the adhesive side of the closure member and the surface of the closure member release liner contacting the adhesive side of the closure member may generally corresponds in size and shape to the closure member. The closure member release liner further may have a first piece and a second piece, the first piece being folded generally perpendicular to the closure member axis and having a tab formed by the fold. The first piece may contact one portion of the closure member adhesive side and the second piece may contact a separate portion of the closure member adhesive side and extend over the first piece. One of the pieces may be released from the closure member without tampering with the other of the pieces. The closure member release liner second piece may also further include a perforation line along the closure member axis.

The anchoring member and closure member fabric layers may be made of a tape, cloth, paper, woven, or non-woven material. The transparent film layer may be made of a polyurethane material. The C-shaped pad may be made of a needle punched rayon material having a polyethylene netting side. The C-shaped pad may have absorbent properties. The closure member pad may be made of a resilient or padding-like material such as a polyurethane foam material or a needle punched rayon material.

A method of using a jugular or subclavian access site dressing in accordance with the present invention includes the steps of: tearing the anchoring member along one of the perforation lines of the anchoring member fabric layer from the edge of the anchoring member fabric layer to the cross stop cut at the end of the perforation line to create a torn perforation line; removing the half of the anchoring member release liner that is opposite from the torn perforation line to expose the adhesive side of the anchoring member fabric layer and film layer; aligning the anchoring member at an access site such that the torn perforation line fits over a side arm of an introducer sheath at the access site, the landmark notches are disposed even with the introducer sheath hub and the anchoring member opening faces away from an anti-contamination shield connector and hub of the introducer sheath; placing the exposed adhesive side of the fabric layer and film layer of the anchoring member onto the skin around the access site that is underneath the aligned anchoring member; removing the other half of the anchoring member release liner to expose the adhesive side of the anchoring member fabric layer and film layer; placing the exposed adhesive side of the anchoring member fabric layer and anchoring member film layer onto the skin while a tab formed between the outer edge of the anchoring member fabric layer and the torn perforation line is pulled underneath the side arm of the introducer sheath in order to seal around the side arm; optionally tearing the closure member along one of the angular perforation lines to optionally remove a wedge from the closure member; removing a half of the part of the closure member release liner that coincides with the angular perforation lines of the closure member to expose approximately one quarter of the adhesive side of the closure member; inserting the closure member under the anti-contamination shield connector and hub, and under any other exposed tubing and/or hubs, such that the pad rests underneath the anti-contamination shield connector, hub, and other tubing/hubs, and the point on the outer edge of the closure member fabric layer and the closure member axis points away from the anchoring member; removing a second half of the part of the closure member release liner that coincides with the angular perforation lines of the closure member and snugging the closure member up firmly to the tubing/hubs; placing the exposed adhesive side of the closure member fabric layer tightly onto the surface below it; removing the other part of the closure member release liner to expose the adhesive side of the closure member fabric layer; and placing the exposed adhesive side of the closure member fabric layer tightly onto the surface below it.

These and other features and advantages of the invention will be more fully understood from the following detailed description of the invention taken together with the accompanying drawings.

BRIEF DESCRIPTION OF THE DRAWINGS

In the drawings:

FIG. 1B is a cross-sectional view of the anchoring member of a dressing as in FIG. 1A;

FIG. 1C is a cross-sectional view of the closure member of a dressing as in FIG. 1A;

FIG. 2 is a perspective view of an embodiment of an anchoring member release liner system of the anchoring member of a dressing as in FIG. 1A;

FIG. 3 is a perspective view of an embodiment of a closure member release liner system of the closure member of a dressing as in FIG. 1A;

FIG. 4B is a cross-sectional view of the anchoring member of a dressing as in FIG. 4A;

FIG. 4C is a cross-sectional view of the closure member of a dressing as in FIG. 4A;

FIG. 5 is a perspective view of an embodiment of an anchoring member release liner system of the anchoring member of a dressing as in FIG. 4A;

FIG. 6 is a perspective view of an embodiment of a closure member release liner system of the closure member of a dressing as in FIG. 4A;

DETAILED DESCRIPTION OF THE INVENTION

Figure 1A:
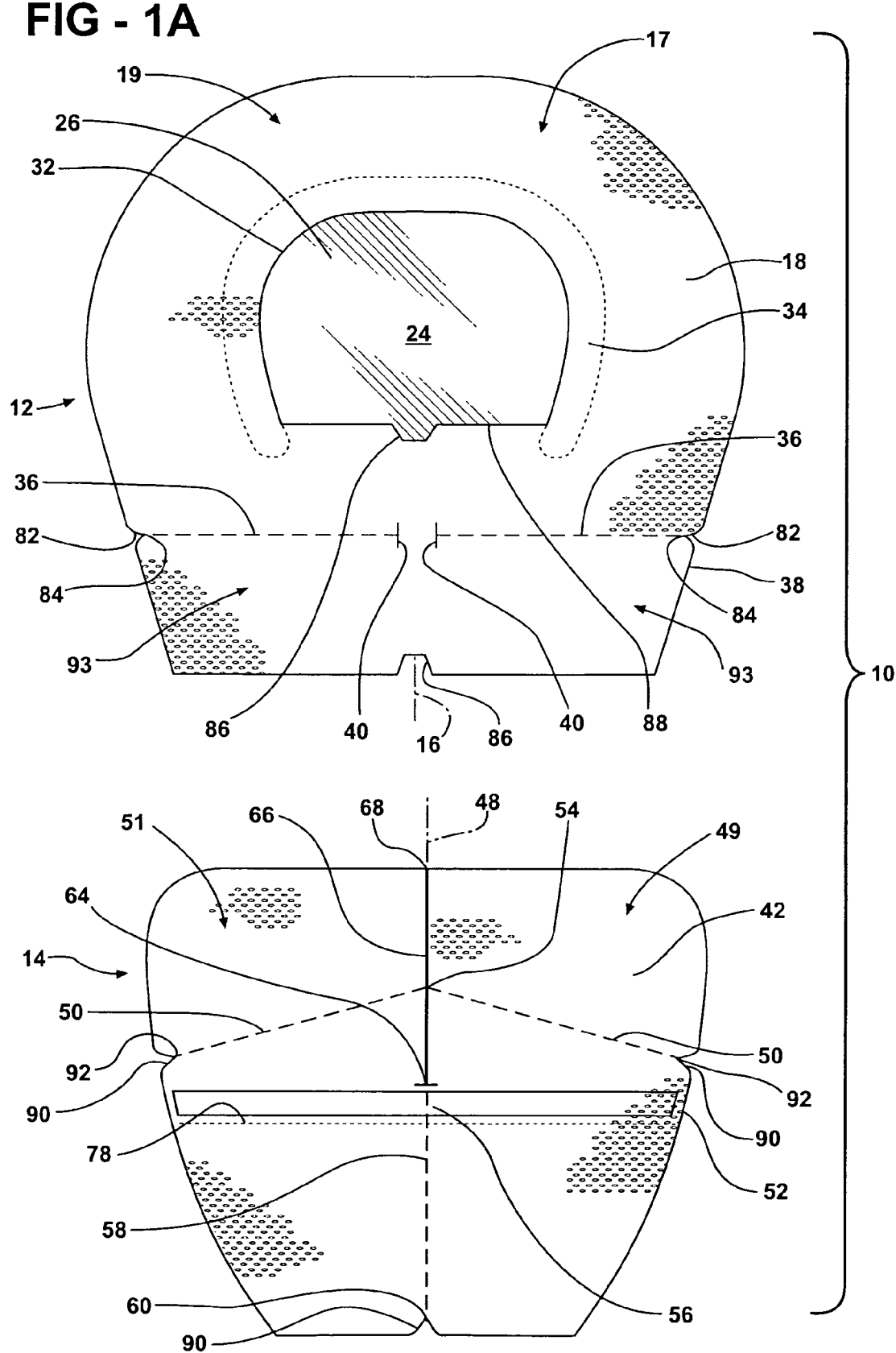
FIG. 1A is a plan view of a two-piece jugular and subclavian access site window dressing in accordance with the present invention including a dressing anchoring member and dressing closure member.

Referring now to the drawings in detail, numeral 10 generally indicates a two-piece jugular and subclavian access site window dressing for the protection of a catheter access site, which is interchangeably usable on both a right or left access site, accommodates various combinations of introducer sheaths and catheters, provides security against detachment from a patient's skin during use, and provides protection against microbial ingress and site or patient systemic infection.

With reference to FIGS. 1A through 1C, in one embodiment the dressing 10 includes an anchoring member 12 and a closure member 14. The anchoring member 12 has an axis 16 that divides the anchoring member 12 into a first portion 17 and a second portion 19. The anchoring member 12 includes a fabric layer 18 having an adhesive side 20 and an opposite non-adhesive side 22. The anchoring member fabric layer 18 may comprise a white spun-lace, non-woven polyester fabric material such as DermaMed Coatings Company, LLC fabric DM 2002 having a medical grade adhesive such as an acrylic adhesive applied thereto. The anchoring member fabric layer 18 may also be any other non-woven material, as well as a tape, cloth, paper, or woven material.

The anchoring member fabric layer 18 has an opening 24 therein to allow viewing therethrough. A transparent film layer 26 closes the opening 24. The transparent film layer 26 is larger in all directions than the opening 24 and includes an adhesive skin adhering side 28 and an opposite non-adhesive side 30. The transparent film layer 26 may comprise a polyurethane material such as DermaMed Coatings Company, LLC DM 4005 having a medical grade adhesive such as an acrylic adhesive applied thereto. The film layer non-adhesive side 30 is adhered onto the adhesive side 20 of the anchoring member fabric layer 18 around the opening 24 and extends beyond the edge 32 of the opening 24. In so extending beyond the edge 32 of the opening 24, the film layer 26 may extend to the edges of the anchoring member fabric layer 18.

With continued reference to FIGS. 1A through 1C, the closure member 14 includes a fabric layer 42 having an adhesive side 44 and an opposite non-adhesive side 46. The closure member fabric layer 42 may comprise a non-woven polyester fabric material such as DermaMed Coatings Company, LLC fabric DM 2092 having a medical grade adhesive such as an acrylic adhesive applied thereto. The closure member fabric layer 42 may also be any other non-woven material, as well as a tape, cloth, paper, or woven material. A closure member axis 48 divides the closure member 14 into a first portion 49 and a second portion 51. The closure member 14 is adapted to overlie and close an end of the anchoring member 12.

Optionally, the anchoring member 12 may further include a generally C-shaped pad 34 disposed along the edge 32 of the opening 24 and generally symmetrically disposed about the anchoring member axis 16. The C-shaped pad 34 may be adhered to the adhesive side 28 of the transparent film layer 26. The C-shaped pad 34 may comprise a needle punched rayon material such as DermaMed Coatings Company, LLC DM 3000 having a polyethylene netting side. The polyethylene netting side is opposite the side of the C-shaped pad 34 that is adhered to the transparent film layer 26. The C-shaped pad 34 provides anti-wrinkling and anti-crumpling support for the anchoring member fabric layer 18 during application of the anchoring member 12 to a jugular or subclavian access site. The C-shaped pad 34 does not have adhesive on a patient skin side. The C-shaped pad 34 also provides circumfluent moisture absorption around the opening 24 keeping the viewing area of the film layer 26 clear and dry of any exudate which may seep from the catheter's percutaneous access sites during use of the dressing.

The anchoring member fabric layer 18 may also have symmetrical perforation lines 36 that extend from an outer edge 38 of the fabric layer 18 towards the anchoring member axis 16. The perforation lines 36 may be generally perpendicular to the anchoring member axis 16 and each may terminate before the anchoring member axis 16 at a cross stop cut 40 that is generally parallel to the anchoring member axis 16. Optionally, perforation lines 36 may extend all the way and join each other at anchor member axis 16 allowing for an entire portion of the anchoring member 12 to be optionally removed. This allows for shortening of the anchoring member 12 for cases where no side arm is present at the access site and wherein a catheter is deeply inserted, hence assisting in getting the catheter access site back into the opening 24 (viewing window).

The closure member 14 may further include a film layer 43 having an adhesive skin adhering side 45 and an opposite non-adhesive side 47. The film layer non-adhesive side 47 is adhered onto the adhesive side 44 of the closure member fabric layer 42. Further, a pad 56 may optionally extend from one edge of the closure member 14 to another edge of the closure member 14 generally perpendicular to the closure member axis 48. The pad 56 may be adhered to the non-adhesive side 46 of the closure member fabric layer 42. The closure member pad 56 may comprise a resilient or padding-like material, for example a needle punched rayon material such as DermaMed Coatings Company, LLC DM 3000 or a polyurethane foam. The pad 56 helps to close any remaining openings under catheters, tubing, and hubs as the closure member 14 is snugged under and around the same before being sealed onto the anchoring member 12.

Symmetrically disposed perforation lines 50 may extend angularly from an outer edge 52 of the closure member 14 towards the closure member axis 48 and meet at a similar point 54 along the closure member axis 48. A perforation line 58 may extend generally centrally from the outer edge 52 of the closure member 14 at a point 60 located on the closure member axis 48, run along the closure member axis 48, and terminate near the center of the closure member 14 at a closure member cross stop cut 64. The closure member cross stop cut 64 may be generally perpendicular to the closure member axis 48. A cut line 66 may extend from the outer edge 52 of the closure member 14 at a point 68 located on the closure member axis 48 opposite the point 60 where the center perforation line 58 begins, and end at the closure member cross stop cut 64.

Further, the dressing 10 may include notches 82 along the outer edge 38 of the anchoring member fabric layer 18 disposed at ends 84 of the anchoring member perforation lines 36 opposite the anchoring member cross stop cuts 40. The anchoring member notches 82 aid the user of the dressing 10 in locating and beginning to tear along the perforation lines 36. Landmark notches 86 may be disposed about the anchoring member axis 16 and may be located at the outer edge 38 of the anchoring member fabric layer 18 and at an edge 88 that does not coincide with the C-shaped pad 34. The landmark notches 86 are useful in aiding the user of the dressing 10 in aligning the anchoring member 12 at the proper spot around the jugular or subclavian access site catheters. Closure member notches 90 may be disposed along the outer edge 52 of the closure member 14 at ends 92 of the closure member perforation lines 50 and at the point 60 on the closure member axis 48 where the closure member center perforation line 58 begins. The closure member notches 90 aid the user of the dressing 10 in beginning to tear along the closure member perforation lines 50 and the closure member center perforation line 58.

As illustrated in FIG. 1B, the dressing 10 may also include an anchoring member release liner 70 having a tackless side 72 contacting the adhesive side 28 of the anchoring member transparent film layer 26. The surface of the anchoring member release liner 70 contacting the adhesive side 28 of the anchoring member film layer 26 may generally correspond in size and shape to the anchoring member fabric layer 18. Optionally, as illustrated in FIG. 2, the anchoring member release liner 70 may be a folded release liner system. The anchoring member release liner 70 may have a first piece 67 and a second piece 69, the first and second pieces being folded along the anchor member axis 16. The anchoring member release liner 70 further including first and second tabs 71, 73 formed by the folds. One of the pieces 67, 69 may be released from the anchoring member 12 without tampering with the other of the pieces, until ready.

As illustrated in FIG. 1C, the dressing 10 may also include a closure member release liner 74 having a tackless side 76 contacting the adhesive side 44 of the closure member fabric layer 42. In the case that the closure member 14 includes a film layer 43, the closure member release liner 74 may contact the film layer adhesive side 45. The surface of the closure member release liner 74 contacting the adhesive side of the closure member 14 generally corresponds in size and shape to the closure member 14. Optionally, as illustrated in FIG. 3, the closure member release liner 74 may be a "fold and flat" release liner system. The closure member release liner 74 may have a first piece 75 and a second piece 77, the first piece 75 being folded generally perpendicular to the closure member axis 48 and having a tab 79 formed by the fold. The first piece 75 contacts one portion 80 of the closure member adhesive side. The second piece 77 contacts a separate portion 81 of the closure member adhesive side and extends over the first piece 75. One of the pieces 75, 77 may be released from the closure member 14 without tampering with the other of the pieces, until ready. The second piece 77 may further include a perforation line 83 along the closure member axis 48, such that one part of the second piece 77 may be removed initially to facilitate routing the closure member 14 under tubing, hubs, etc. without crumpling or wrinkling the closure member via the closure member adhering to itself.

Figure 4A:
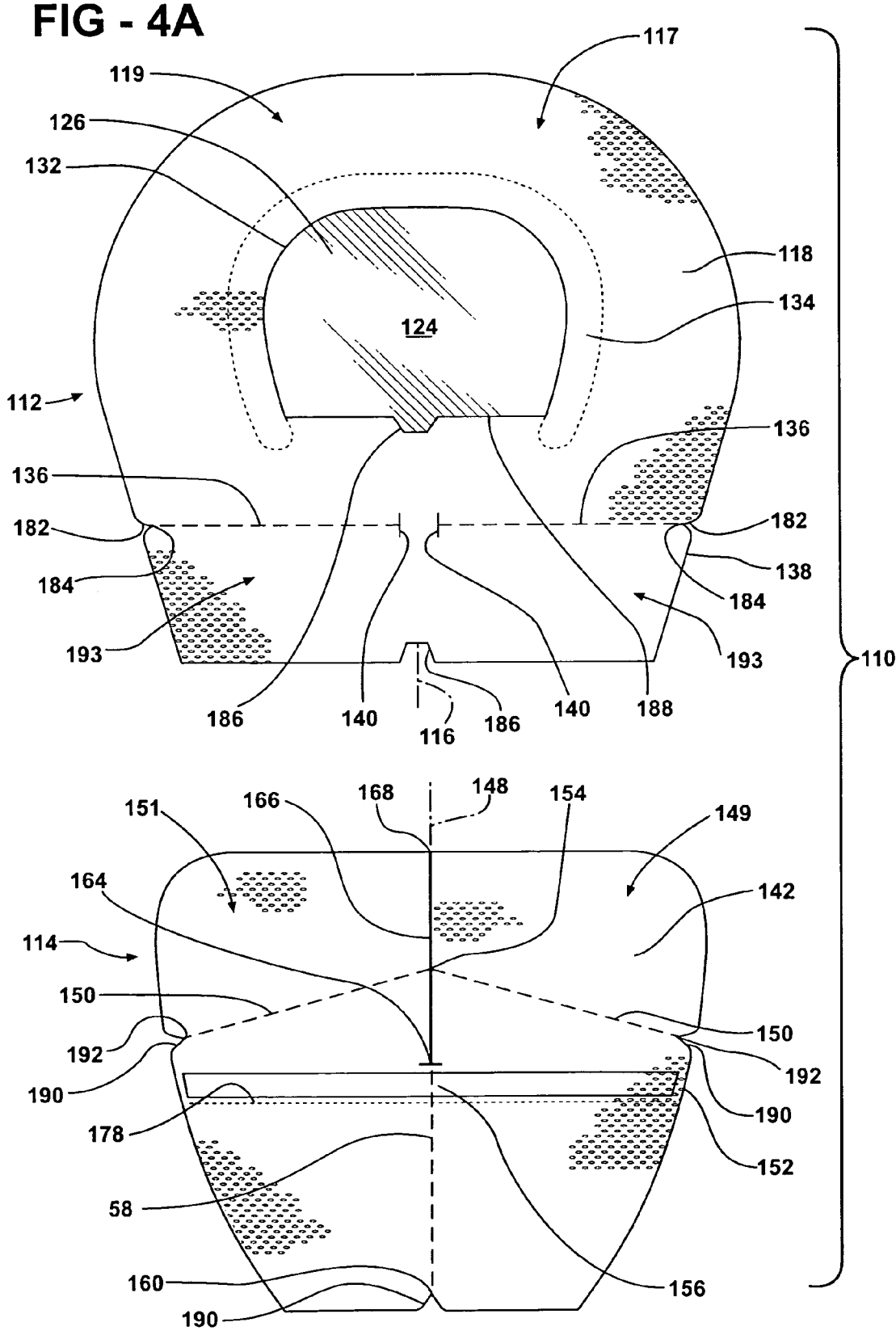
FIG. 4A is a plan view of an alternative embodiment of a two-piece jugular and subclavian access site window dressing in accordance with the present invention including a dressing anchoring member and dressing closure member.

With reference now to FIGS. 4A through 4C, in an alternative embodiment the dressing 110 includes an anchoring member 112 and a closure member 114. The anchoring member 112 has a symmetry axis 116 that divides the anchoring member 112 into two generally symmetrical halves, namely a first half portion 117 and a second half portion 119. The symmetry of the anchoring member 112 allows the anchoring member to be used on either a right access site or a left access site. The anchoring member 112 includes a fabric layer 118 having an adhesive side 120 and an opposite non-adhesive side 122.

The anchoring member fabric layer 118 has an opening 124 therein to allow viewing therethrough. A transparent film layer 126 closes the opening 124. The transparent film layer 126 is larger in all directions than the opening 124 and includes an adhesive skin adhering side 128 and an opposite non-adhesive side 130. The film layer non-adhesive side 130 is adhered onto the adhesive side 120 of the anchoring member fabric layer 118 around the opening 124 and extends beyond the edge 132 of the opening 124. In so extending beyond the edge 132 of the opening 124, the film layer 126 may extend to the edges of the anchoring member fabric layer 118.

The anchoring member 112 further includes a generally C-shaped pad 134 disposed along the edge 132 of the opening 124 and generally symmetrically disposed about the anchoring member symmetry axis 116. The C-shaped pad 134 is adhered to the adhesive side 128 of the transparent film layer 126. The C-shaped pad 134 provides anti-wrinkling and anti-crumpling support for the anchoring member fabric layer 218 during application of the anchoring member 212 to a jugular access site. The C-shaped pad 134 does not have adhesive on a patient skin side. Also, the C-shaped pad 134 also provides circumfluent moisture absorption around the opening 124 keeping the viewing area of the film layer 126 clear and dry of any exudate which may seep from the catheter's percutaneous access sites during use of the dressing.

The anchoring member fabric layer 118 also includes symmetrically disposed perforation lines 136 that extend from an outer edge 138 of the fabric layer 118 towards the anchoring member symmetry axis 116. The perforation lines 136 are generally perpendicular to the anchoring member symmetry axis 116 and each terminates before the anchoring member symmetry axis 116 at a cross stop cut 140 that is generally parallel to the anchoring member symmetry axis 116. Optionally, perforation lines 136 may extend all the way and join each other at anchor member axis 116 allowing for an entire portion of the anchoring member 112 to be optionally removed. This allows for shortening of the anchoring member 112 for cases where no side arm is present at the access site and wherein a catheter is deeply inserted, hence assisting in getting the catheter access site back into the opening 124 (viewing window).

The closure member 114 includes a fabric layer 142 having an adhesive side 144 and an opposite non-adhesive side 146. A closure member symmetry axis 148 divides the closure member 114 into two generally symmetrical halves, namely a first half portion 149 and a second half portion 151. The symmetry of the closure member 114 allows the closure member to be used on either a right access site or a left access site. The closure member further includes a film layer 143 having an adhesive skin adhering side 145 and an opposite non-adhesive side 147, said film layer non-adhesive side 147 being adhered onto the adhesive side 144 of said closure member fabric layer 142.

Symmetrically disposed perforation lines 150 extend angularly from an outer edge 152 of the closure member 114 towards the closure member symmetry axis 148 and meet at a similar point 154 along the closure member symmetry axis 148. A perforation line 158 extends generally centrally from the outer edge 152 of the closure member 114 at a point 160 located on the closure member symmetry axis 148, runs along the closure member symmetry axis 148, and terminates near the center of the closure member 114 at a closure member cross stop cut 164. The closure member cross stop cut 164 is generally perpendicular to the closure member symmetry axis 148. A cut line 166 extends from the outer edge 152 of the closure member 114 at a point 168 located on the closure member symmetry axis 148 opposite the point 160 where the center perforation line 158 begins, and ends at the closure member cross stop cut 164.

Optionally, the closure member 114 further may include a pad 156 extending from one edge of the closure member 114 to another edge of the closure member 114 generally perpendicular to the closure member symmetry axis 148. The pad 156 may be adhered to the non-adhesive side 146 of the closure member fabric layer 142. The pad 156 helps to close any remaining openings under catheters, tubing, and hubs as the closure member 114 is snugged under and around the same before being sealed onto the anchoring member 112.

Further, the dressing 110 may include notches 182 along the outer edge 138 of the anchoring member fabric layer 118 disposed at ends 184 of the anchoring member perforation lines 136 opposite the anchoring member cross stop cuts 140. The anchoring member notches 182 aid the user of the dressing 110 in locating and beginning to tear along the perforation lines 136. Landmark notches 186 may be disposed about the anchoring member symmetry axis 116 and may be located at the outer edge 138 of the anchoring member fabric layer 118 and at an edge 188 that does not coincide with the C-shaped pad 134. The landmark notches 186 are useful in aiding the user of the dressing 110 in aligning the anchoring member 112 at the proper spot around the jugular access site catheters. Closure member notches 190 may be disposed along the outer edge 152 of the closure member 114 at ends 192 of the closure member perforation lines 150 and at the point 160 on the closure member symmetry axis 148 where the closure member center perforation line 158 begins. The closure member notches 190 aid the user of the dressing 110 in beginning to tear along the closure member perforation lines 150 and the closure member center perforation line 158.

Further, as illustrated in FIG. 4B, the dressing 110 may include an anchoring member release liner 170 having a tackless side 172 contacting the adhesive side 128 of the anchoring member transparent film layer 126 and the C-shaped pad 134. The surface of the anchoring member release liner 170 contacting the adhesive side 128 of the anchoring member film layer 126 may generally correspond in size and shape to the anchoring member fabric layer 118. Optionally, as illustrated in FIG. 5, the anchoring member release liner 170 may be a folded release liner system. The anchoring member release liner 170 may have a first piece 167 and a second piece 169, the first and second pieces being folded along the anchor member symmetry axis 116. The anchoring member release liner 170 further including first and second tabs 171, 173 formed by the folds. One of the pieces 167, 169 may be released from the anchoring member 112 without tampering with the other of the pieces, until ready.

The dressing 110, as illustrated in FIG. 4C, may also include a closure member release liner 174 having a tackless side 176 contacting the adhesive side 145 of the closure member film layer 143. The surface of the closure member release liner 174 contacting the adhesive side 145 of the closure member 114 generally corresponds in size and shape to the closure member 114. Optionally, as illustrated in FIG. 6, the closure member release liner 174 may be a "fold and flat" release liner system. The closure member release liner 174 may have a first piece 175 and a second piece 177, the first piece 175 being folded generally perpendicular to the closure member symmetry axis 148 and having a tab 179 formed by the fold. The first piece 175 contacts one portion 180 of the closure member adhesive side 145. The second piece 177 contacts a separate portion 181 of the closure member adhesive side 145 and extends over the first piece 175. One of the pieces 175, 177 may be released from the closure member 114 without tampering with the other of the pieces, until ready. The second piece 177 may further include a perforation line 183 along the closure member symmetry axis 148, such that one part of the second piece 177 may be removed initially to facilitate routing the closure member 114 under tubing, hubs, etc. without crumpling or wrinkling the closure member via the closure member adhering to itself.

Figure 7:
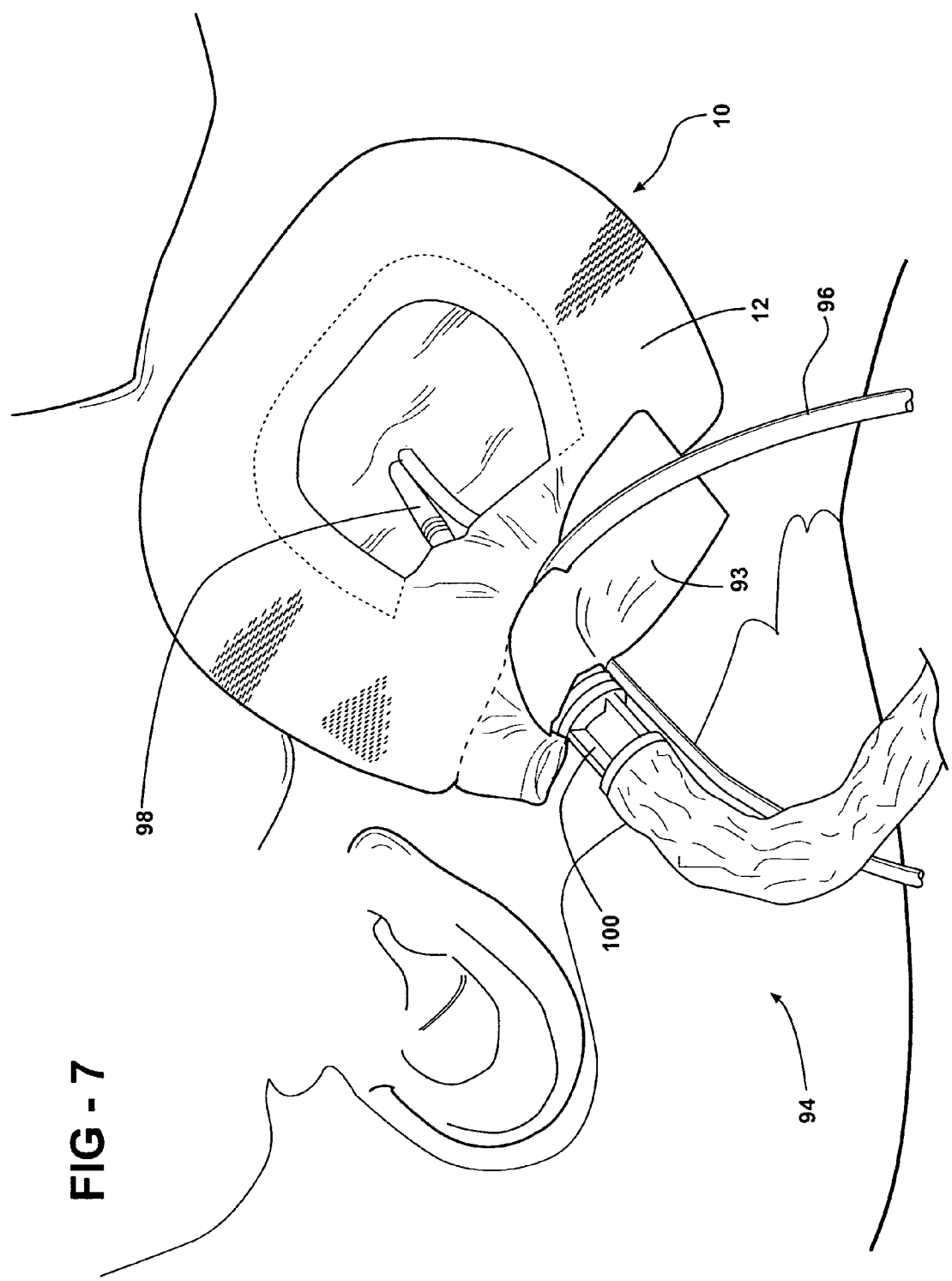
FIG. 7 is an environmental view of the anchoring member of the jugular and subclavian access site dressing of FIG. 1A.
Figure 8:
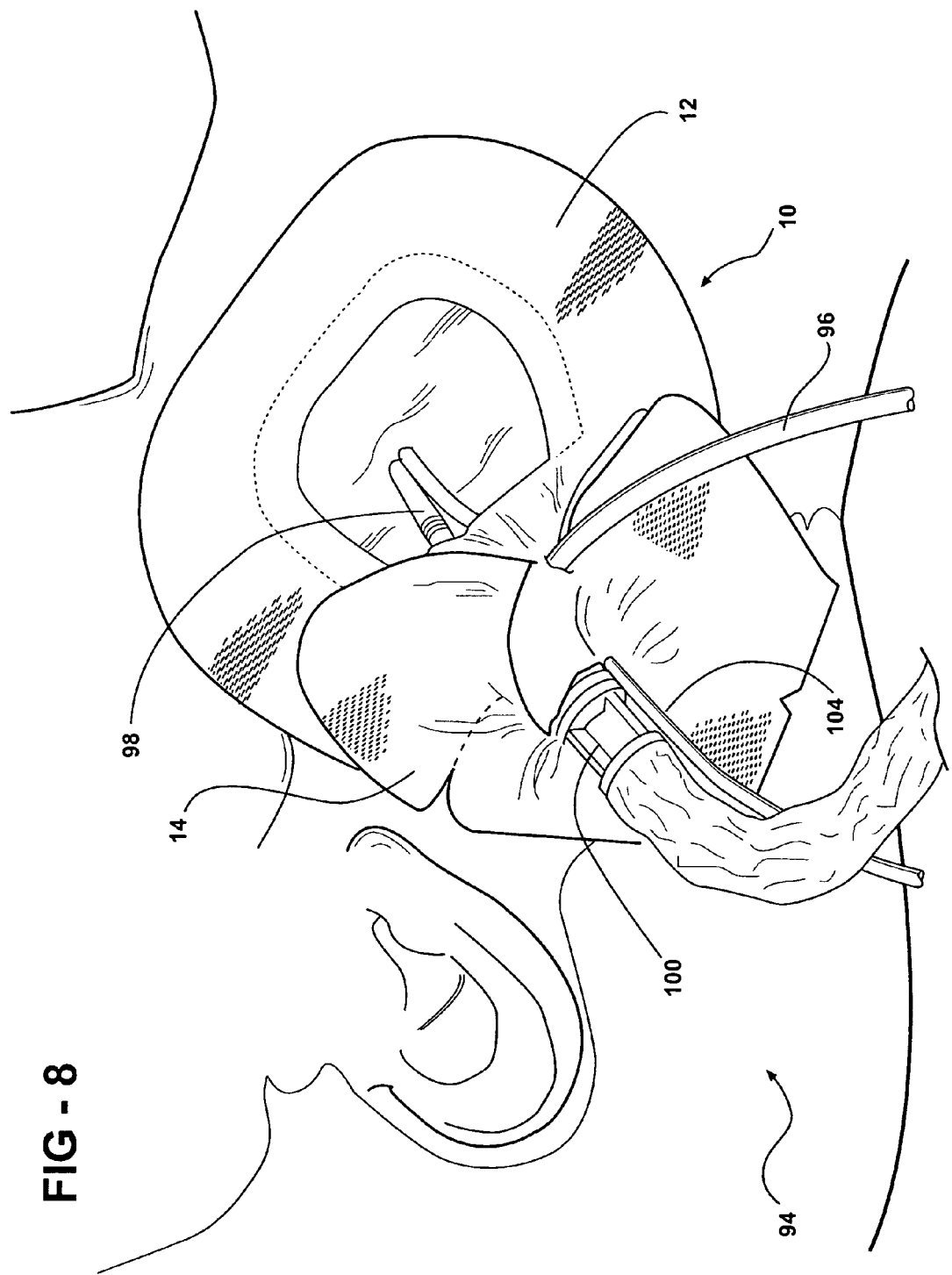
FIG. 8 is an environmental view of the anchoring member and the closure member of the jugular and subclavian access site dressing of FIG. 1A.

FIGS. 7 and 8 show clinical environmental views of the jugular and subclavian access site dressing 10 in use at a jugular access site. With reference to FIGS. 1A, 1B, and 7, the anchoring member 12 of the dressing 10 has been applied to a right-hand side jugular access site of a patient 94. In order to have applied the anchoring member 12 as shown in FIG. 7, the anchoring member 12 was torn along first portion 17 perforation line 36 up to the cross stop cut 40 for application on the right-hand side jugular access site. In the alternative, if the dressing 10 were to be applied to a left-hand side jugular access site, then the second portion 19 perforation line 36 would have been torn instead. The portion of the anchoring member release liner 70 that is opposite from the first portion 17 perforation line 36 (which is the piece of the anchoring member release liner 70 corresponding to the second portion 19 of the anchoring member fabric layer 18) was then removed to expose the adhesive side 20 of the anchoring member fabric layer 18 and/or the adhesive side 28 of the transparent film layer 26. Again, if the dressing 10 were to be applied to the left-hand side jugular access site, then the half of the anchoring member release liner 70 that corresponds to the first portion 17 of the anchoring member fabric layer 18 would have been removed instead.

Next, the anchoring member 12 was aligned at the jugular access site such that the torn perforation line 36 fitted over a side arm 96 of an introducer sheath 98 at the jugular access site, the landmark notches 86 were even with the introducer sheath 98, and the anchoring member 12 faced away from an anti-contamination hub 100 of the introducer sheath 98. The exposed adhesive side 28 of the film layer 26 was then placed onto the skin around the jugular access site that was underneath the aligned anchoring member 12. Next, the remaining half of the anchoring member release liner 70 was removed to expose the adhesive side 20 of the anchoring member fabric layer 18 and/or the adhesive side 28 of the film layer 26. The exposed adhesive side 28 of the film layer 26 was then placed onto the skin while a tab 93 formed between the outer edge 38 of the anchoring member fabric layer 18 and the torn perforation line 36 was pulled underneath the side arm 96 in order to seal around the side arm 96.

With reference to FIGS. 1A, 1C, and 8, the closure member 14 of the dressing 10 has also been applied to the right-hand side jugular access site of the patient 94, partially covering the anchoring member 12. The closure member 14 is applied after application of the anchoring member 12. In order to apply the closure member 14 as shown in FIG. 8, the closure member 14 was optionally torn along the first portion 49 perforation line 50 up to the end point 54 for application on the right-hand side jugular access site. In the alternative, if the dressing 10 were to be applied to the left-hand side jugular access site, then the second portion 51 angular perforation line 50 optionally would have been torn instead. Next, a first half of the part of the closure member release liner 74 that coincides with the angular perforation lines 50 of the closure member 14 was removed to expose approximately one quarter of the adhesive side 45 of the closure member film layer 43.

Further, the closure member 14 was inserted under the anti-contamination hub 100 and any other exposed tubing 104 such that the optional closure member pad 56 rests underneath the anti-contamination hub 100 and the point 60 on the outer edge 52 of the closure member fabric layer 42 and the closure member symmetry axis 48 points away from the anchoring member 12. Next, a second half of the part of the closure member release liner 74 that coincides with the angular perforation lines 50 of the closure member 14 was removed. Then, after snugging the closure member 12 around the tubing/hubs, the exposed adhesive side 45 of the closure member film layer 43 was placed tightly onto the surface below it. Next, the remaining part of the closure member release liner 74 was removed to expose the adhesive side 44 of the closure member fabric layer 42. Finally, the exposed adhesive side 45 of the closure member film layer 43 was placed tightly onto the surface below it.

Subsequent removal of the dressing 10 is simple due to the design of the dressing. The anchoring member 12 and closure member 14 of the dressing 10 may be removed simultaneously without unsealing the overlaps between the two members. First, the end of the closure member 12 around the point 60 is lifted off of the skin of the patient 94. Then the perforation line 58 beginning at the point 60 is separated all the way through the pad 56 to the cross stop cut 64. Finally, the catheters, tubing, hubs, etc. is grasped and steadied while the adhesively combined anchoring member 12 and closure member 14 are peeled off the catheters, hubs, etc. access site as well as the surrounding skin of the patient 94.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A jugular and subclavian access site window dressing for the protection of a jugular or subclavian catheter access site, which is interchangeably usable on both a right or left access site and provides security against detachment from a patient's skin during use, the dressing comprising:

an anchoring member and a closure member;
said anchoring member having an axis that divides said anchoring member into first and second portions;
said anchoring member comprising an anchoring member fabric layer having an adhesive side and an opposite non-adhesive side;
said anchoring member fabric layer having an opening therein bounded by an edge, to allow access site viewing through said opening, and further including symmetrically disposed perforation lines extending from an outer edge of said anchoring member fabric layer towards said anchoring member axis and being generally perpendicular to said anchoring member axis;
said anchoring member further comprising a transparent film layer having an adhesive skin adhering side and an opposite non-adhesive side, said film layer being larger than said opening in all directions and closing said opening in said anchoring member fabric layer; said film layer non-adhesive side being adhered onto the adhesive side of said anchoring member fabric layer around said opening such that said transparent film layer extends beyond said edge of said opening;
said closure member having an axis that divides said closure member into first and second portions; and
said closure member comprising a closure member fabric layer having an adhesive side and an opposite non-adhesive side;
said closure member being adapted to overlie and close an end of said anchoring member.

2. A jugular and subclavian access site dressing as in claim 1, wherein each perforation line terminates before said anchoring member axis at a cross stop cut, said cross stop cut being generally parallel to said anchoring member axis.

3. A jugular and subclavian access site dressing as in claim 1, further comprising notches along the outer edge of said anchoring member fabric layer disposed at ends of said anchoring member perforation lines.

4. A jugular and subclavian access site dressing as in claim 1, wherein said anchoring member further comprises a generally C-shaped pad disposed along said edge of said opening and generally symmetrically disposed about said anchoring member axis, said C-shaped pad being adhered to said adhesive side of said film layer.

5. A jugular and subclavian access site dressing as in claim 1, wherein said closure member further comprises a film layer having an adhesive skin adhering side and an opposite non-adhesive side, said film layer non-adhesive side being adhered onto the adhesive side of said closure member fabric layer.

6. A jugular and subclavian access site dressing as in claim 1, wherein said closure member further comprises symmetrically disposed perforation lines extending angularly from an outer edge of said closure member towards said closure member axis and meeting at a similar point along said closure member axis.

7. A jugular and subclavian access site dressing as in claim 6, further comprising notches along the outer edge of said closure member disposed at ends of said closure member perforation lines.

8. A jugular and subclavian access site dressing as in claim 1, wherein said closure member further comprises a perforation line extending generally centrally from an outer edge of said closure member at a point located on said closure member axis, running along said closure member axis, and terminating near the center of said closure member.

9. A jugular and subclavian access site dressing as in claim 8, wherein said closure member center perforation line terminates at a closure member cross stop cut, said cross stop cut being generally perpendicular to said closure member axis.

10. A jugular and subclavian access site dressing as in claim 8, further comprising a notch at said point on said closure member axis where said closure member center perforation line begins.

11. A jugular and subclavian access site dressing as in claim 1, wherein said closure member further comprises a cut line extending generally centrally from an outer edge of said closure member at a point located on said closure member axis.

12. A jugular and subclavian access site dressing as in claim 1, wherein said anchoring member fabric layer has landmark notches disposed about said anchoring member axis and being located both at the outer edge of said anchoring member fabric layer and at an edge of said opening.

13. A jugular and subclavian access site dressing as in claim 1, further comprising an anchoring member release liner having a tackless side contacting said adhesive side of said anchoring member film layer; wherein the surface of said anchoring member release liner contacting said adhesive side of said anchoring member film layer generally corresponds in size and shape to said anchoring member fabric layer.

14. A jugular and subclavian access site dressing as in claim 13, wherein said anchoring member release liner has a first piece and a second piece; said first and second pieces being folded along said anchor member axis; said anchoring member release liner further including first and second tabs formed by said folds; whereby one of said pieces can be released from said anchoring member without tampering with the other of said pieces.

15. A jugular and subclavian access site dressing as in claim 1, further comprising a closure member release liner having a tackless side contacting said adhesive side of said closure member; wherein the surface of said closure member release liner contacting said adhesive side of said closure member generally corresponds in size and shape to said closure member.

16. A jugular and subclavian access site dressing as in claim 15, wherein said closure member release liner has a first piece and a second piece; said first piece being folded generally perpendicular to said closure member axis and having a tab formed by said fold; said first piece contacting one portion of the closure member adhesive side; said second piece contacting a separate portion of the closure member adhesive side and extending over said first piece; whereby one of said pieces can be released from said closure member without tampering with the other of said pieces.

17. A jugular and subclavian access site dressing as in claim 16, wherein said closure member release liner second piece includes a perforation line along said closure, member axis.

18. A jugular and subclavian access site dressing as in claim 1, further comprising a pad disposed about said closure member axis generally perpendicular to said closure member axis.

19. A jugular and subclavian access site dressing as in claim 18, wherein said pad extends from one edge of said closure member to another edge of said closure member.

20. A jugular and subclavian access site dressing as in claim 1, wherein said anchoring member fabric layer comprises one of a tape, cloth, paper, woven, and non-woven material.

21. A jugular and subclavian access site dressing as in claim 1, wherein said transparent film layer comprises a polyurethane material.

22. A jugular and subclavian access site dressing as in claim 1, wherein said closure member fabric layer comprises one of a tape, cloth, paper, woven, and non-woven material.

23. A jugular and subclavian access site dressing as in claim 4, wherein said C-shaped pad is a needle punched rayon material having a polyethylene netting side.

24. A jugular and subclavian access site dressing as in claim 18, wherein said pad is one of a polyurethane foam material and a needle punched rayon material.

25. A jugular and subclavian access site window dressing for the protection of a jugular catheter access site, which is interchangeably usable on both a right or left access site and provides security against detachment from a patient's skin during use, the dressing comprising:
an anchoring member and a closure member;
said anchoring member having a symmetry axis that divides said anchoring member into generally symmetrical right and left half portions;
said anchoring member comprising an anchoring member fabric layer having an adhesive side and an opposite non-adhesive side;
said anchoring member fabric layer having an opening therein bounded by an edge, to allow access site viewing through said opening;
said anchoring member fabric layer also having symmetrically disposed perforation lines extending from an outer edge of said anchoring member fabric layer towards said anchoring member symmetry axis and being generally perpendicular to said anchoring member symmetry axis and each perforation line terminating before said anchoring member symmetry axis at a cross stop cut;
said cross stop cut being generally parallel to said anchoring member symmetry axis;
said anchoring member further comprising a transparent film layer having an adhesive skin adhering side and an opposite non-adhesive side, said film layer being larger than said opening in all directions and closing said opening in said anchoring member fabric layer; said film layer non-adhesive side being adhered onto the adhesive side of said anchoring member fabric layer around said opening such that said transparent film layer extends beyond said edge of said opening;
said anchoring member further comprising a C-shaped pad disposed along said edge of said opening and generally symmetrically disposed about said anchoring member symmetry axis, said C-shaped pad being adhered to said adhesive side of said film layer;
said closure member having a symmetry axis that divides said closure member into generally symmetrical right and left half portions;
said closure member comprising a closure member fabric layer having an adhesive side and an opposite non-adhesive side;
said closure member further comprising a film layer having an adhesive skin adhering side and an opposite non-adhesive side, said film layer non-adhesive side being adhered onto the adhesive side of said closure member fabric layer;
said closure member also having symmetrically disposed perforation lines extending angularly from an outer edge of said closure member towards said closure member symmetry axis and meeting at a similar point along said closure member symmetry axis;
said closure member further comprising a perforation line extending generally centrally from said outer edge of said closure member at a point located on said closure member symmetry axis, running along said closure member symmetry axis, and terminating near the center of said closure member at a closure member cross stop cut, said closure member cross stop cut being generally perpendicular to said closure member symmetry axis; and said closure member further comprising a cut line extending generally centrally from said outer edge of said closure member at a point located on said closure member symmetry axis opposite said point where said center perforation line begins, and ending at said closure member cross stop cut;

said closure member being adapted to overlie and close an end of said anchoring member.

26. A jugular and subclavian access site dressing as in claim 25, further comprising an anchoring member release liner having a tackless side contacting said adhesive side of said anchoring member film layer and said C-shaped pad; wherein the surface of said anchoring member release liner contacting said adhesive side of said anchoring member film layer generally corresponding in size and shape to said anchoring member fabric layer.

27. A jugular and subclavian access site dressing as in claim 26, wherein said anchoring member release liner has a first piece and a second piece; said first and second pieces being folded along said anchor member symmetry axis; said anchoring member release liner further including first and second tabs formed by said folds; whereby one of said pieces can be released from said anchoring member without tampering with the other of said pieces.

28. A jugular and subclavian access site dressing as in claim 25, further comprising notches along the outer edge of said anchoring member fabric layer disposed at ends of said anchoring member perforation lines opposite said anchoring member cross stop cuts.

29. A jugular and subclavian access site dressing as in claim 25, wherein said anchoring member fabric layer has landmark notches disposed about said anchoring member symmetry axis and being located both at the outer edge of said anchoring member fabric layer and at an edge of said opening that does not coincide with said C-shaped pad.

30. A jugular and subclavian access site dressing as in claim 25, further comprising a closure member release liner having a tackless side contacting said adhesive side of said closure member film layer; wherein the surface of said closure member release liner contacting said adhesive side of said closure member film layer generally corresponds in size and shape to said closure member.

31. A jugular and subelavian access site dressing as in claim 30, wherein said closure member release liner has a first piece and a second piece; said first piece being folded generally perpendicular to said closure member symmetry axis and having a tab formed by said fold; said first piece contacting one portion of the closure member adhesive side; said second piece contacting a separate portion of the closure member adhesive side and extending over said first piece; whereby one of said pieces can be released from said anchoring member without tampering with the other of said pieces.

32. A jugular and subclavian access site dressing as in claim 31, wherein said closure member release liner second piece includes a perforation line along said closure member symmetry axis.

33. A jugular and subclavian access site dressing as in claim 25, further comprising a pad disposed about said closure member symmetry axis near the center of said closure member and adhered to the non-adhesive side of said closure member fabric layer.

34. A jugular and subclavian access site dressing as in claim 33, wherein said pad extends from one edge of said closure member to another edge of said closure member.

35. A jugular and subclavian access site dressing as in claim 25, further comprising notches along the outer edge of said closure member disposed at ends of said closure member perforation lines and at said point on said closure member symmetry axis where said closure member center perforation line begins.

36. A method of using a jugular and subclavian access site window dressing for the protection and visualization of a catheter access site wherein a catheter or other medical tubing enters a patient through the skin that is usable on either a right or left access site and provides security against detachment of the dressing from a patient's skin during use, comprising the step of:

providing a jugular and subclavian access site window dressing comprising:

an anchoring member and a closure member;

said anchoring member having an axis that divides said anchoring member into first and second portions;

said anchoring member comprising an anchoring member fabric layer having an adhesive side and an opposite non-adhesive side;

said anchoring member fabric layer having an opening therein bounded by an edge, to allow access site viewing through said opening, and further including symmetrically disposed perforation lines extending from an outer edge of said anchoring member fabric layer towards said anchoring member axis and being generally perpendicular to said anchoring member axis;

said anchoring member further comprising a transparent film layer having an adhesive skin adhering side and an opposite non-adhesive side, said film layer being larger than said opening in all directions and closing said opening in said anchoring member fabric layer; said film layer non-adhesive side being adhered onto the adhesive side of said anchoring member fabric layer around said opening such that said transparent film layer extends beyond said edge of said opening;

said closure member having an axis that divides said closure member into first and second portions; and said closure member comprising a closure member fabric layer having an adhesive side and an opposite non-adhesive side;

said closure member being adapted to overlie and close an end of said anchoring member.

37. The method of claim 36, wherein the step of providing a jugular and subclavian access site window dressing further comprises providing an access site window dressing in which:

each of said perforation lines terminates before said anchoring member axis at a cross stop cut;

said cross stop cut is generally parallel to said anchoring member axis;

said anchoring member further comprises a C-shaped pad disposed along said edge of said opening and generally symmetrically disposed about said anchoring member axis, said C-shaped pad being adhered to said adhesive side of said film layer;

said anchoring member fabric layer has landmark notches disposed about said anchoring member axis and being located both at the outer edge of said anchoring member fabric layer and at an edge of said opening that does not coincide with said C-shaped pad;

said closure member has symmetrically disposed perforation lines extending angularly from an outer edge of said closure member towards said closure member axis and meeting at a similar point along said closure member axis;

said closure member further comprises a film layer having an adhesive skin adhering side and an opposite non-adhesive side, said film layer non-adhesive side being adhered onto the adhesive side of said closure member fabric layer;

said closure member further comprises a pad disposed about said closure member axis generally perpendicular to said closure member axis;

said closure member further comprises a perforation line extending generally centrally from said outer edge of said closure member at a point located on said closure member axis, running along said closure member axis, and terminating near the center of said closure member at a closure member cross stop cut, said closure member cross stop cut being perpendicular to said closure member axis; and said closure member further comprises a cut line extending generally centrally from said outer edge of said closure member at a point located on said closure member axis opposite said point where said center perforation line begins, and ending at said closure piece cross stop cut.

38. The method of claim 37, wherein the step of providing a jugular and subclavian access site window dressing further comprises providing an access site window dressing having:

an anchoring member release liner having a tackless side contacting said adhesive side of said anchoring member film layer and said C-shaped pad; wherein the surface of said anchoring member release liner contacting said adhesive side of said anchoring member film layer generally corresponds in size and shape to said anchoring member fabric layer; said anchoring member release liner further having a first piece and a second piece; said first and second pieces being folded along said anchor member axis; said anchoring member release liner further including first and second tabs formed by said folds; whereby one of said pieces can be released from said anchoring member without tampering with the other of said pieces; and a closure member release liner having a tackless side contacting said adhesive side of said closure member film layer; wherein the surface of said closure member release liner contacting said adhesive side of said closure member generally corresponds in size and shape to said closure member; said closure member release liner further having a first piece and a second piece; said first piece being folded generally perpendicular to said closure member axis and having a tab formed by said fold; said first piece contacting one portion of the closure member adhesive side; said second piece contacting a separate portion of the closure member adhesive side and extending over said first piece.

39. The method of claim 38, further comprising the steps of:

tearing the anchoring member along one of the perforation lines of the anchoring member fabric layer from the edge of the anchoring member fabric layer to the cross stop cut at the end of the perforation line being torn to create a torn perforation line;

removing the half of the anchoring member release liner that is opposite from the torn perforation line to expose the adhesive side of the anchoring member film layer;

aligning the anchoring member at an access site such that the torn perforation line fits over a side arm of an introducer sheath at the access site, the landmark notches are disposed even with the introducer sheath and the anchoring member faces away from an anti-contamination hub of the introducer sheath;

placing the exposed adhesive side of the film layer of the anchoring member onto the skin around the access site that is underneath the aligned anchoring member;

removing the other half of the anchoring member release liner to expose the adhesive side of the anchoring member film layer;

placing the exposed adhesive side of the anchoring member film layer onto the skin while a tab formed between the outer edge of the anchoring member fabric layer and the torn perforation line is pulled underneath the side arm of the introducer sheath in order to seal around the side arm;

tearing the closure member along one of the angular perforation lines to remove a wedge from the closure member;

removing the part of the closure member release liner that coincides with the angular perforation lines of the closure member to expose the adhesive side of the closure piece film layer;

inserting the closure member under the anti-contamination hub and under any other exposed tubing such that the pad rests underneath the anti-contamination hub and the point on said outer edge of said closure member and said closure member axis points away from the anchoring member;

placing the exposed adhesive side of the closure member film layer tightly onto the surface below it;

removing the other part of the closure member release liner to expose the adhesive side of the closure member film layer; and placing the exposed adhesive side of the closure member film layer tightly onto the surface below it.

* * * * *